US009476694B2

(12) United States Patent
Dubois et al.

(10) Patent No.: US 9,476,694 B2
(45) Date of Patent: Oct. 25, 2016

(54) OPTICAL METHOD FOR CHARACTERIZING TRANSPARENT PARTICLES

(75) Inventors: Frank Dubois, Brussels (BE); Catherine Yourassowsky, Brussels (BE)

(73) Assignee: Universite Libre de Bruxelles, Brussels (BE)

( * ) Notice: Subject to any disclaimer, the term of this patent is extended or adjusted under 35 U.S.C. 154(b) by 57 days.

(21) Appl. No.: 13/884,508

(22) PCT Filed: Nov. 9, 2011

(86) PCT No.: PCT/EP2011/069746
§ 371 (c)(1),
(2), (4) Date: Jul. 25, 2013

(87) PCT Pub. No.: WO2012/062805
PCT Pub. Date: May 18, 2012

(65) Prior Publication Data
US 2013/0308135 A1    Nov. 21, 2013

(30) Foreign Application Priority Data

Nov. 12, 2010  (EP) .................................... 10190977
Apr. 11, 2011  (EP) .................................... 11161884

(51) Int. Cl.
*G01N 21/59*     (2006.01)
*G01B 9/021*     (2006.01)
(Continued)

(52) U.S. Cl.
CPC ............. *G01B 9/021* (2013.01); *G01N 21/59* (2013.01); *G03H 1/00* (2013.01); *G03H 1/0005* (2013.01);
(Continued)

(58) Field of Classification Search
CPC .............. G01B 9/021; G01N 21/59; G03H 2001/0033; G03H 2001/005; G03H 1/0866; G03H 1/00; G11B 7/0065
USPC ........................................ 356/335–343, 457
See application file for complete search history.

(56) References Cited

U.S. PATENT DOCUMENTS 4,739,177 A  *  4/1988  Borden ........................ 250/574
5,633,503 A  *  5/1997  Kosaka ..................... 250/458.1
(Continued)

FOREIGN PATENT DOCUMENTS

EP          1399730 A2    3/2004
EP        1 631 788 A1    3/2006
(Continued)

OTHER PUBLICATIONS

Frank Dubois et al.; Dark-field Digital Holographic Microscopy to Investigate Objects that are Nanosized or Smaller than the Optical Resolution; Optics Letters; Nov. 15, 2008; 3 pages (2605-2607); vol. 33, No. 22.
(Continued)

*Primary Examiner* — Hoa Pham
(74) *Attorney, Agent, or Firm* — Reinhart Boerner Van Deuren P.C.

(57) ABSTRACT

The present invention is related to a method for characterizing transparent objects (2, 3) in a transparent medium (1), said transparent objects (2, 3) presenting an optical focal area (5, 6) said method comprising the steps of: illuminating a sample comprising the objects (2, 3) to be characterized by means of a directional light (7) source, thereby inducing light intensity peaks (5, 6) at the focal area of said transparent objects; determining at least one characteristic of the light intensity peak (5, 6) induced by said object to be characterized, determining from said light intensity peak (5, 6) at least one property of said object.

19 Claims, 3 Drawing Sheets

(51) Int. Cl.
*G03H 1/00* (2006.01)
*G03H 1/04* (2006.01)

(52) U.S. Cl.
CPC ..... *G03H 2001/005* (2013.01); *G03H 2001/0033* (2013.01); *G03H 2001/0445* (2013.01); *G03H 2210/55* (2013.01); *G03H 2222/24* (2013.01)

(56) References Cited

U.S. PATENT DOCUMENTS

| | | | |
|---|---|---|---|
| 5,710,069 A * | 1/1998 | Farkas et al. | 438/7 |
| 5,882,863 A * | 3/1999 | Imai et al. | 435/6.12 |
| 7,009,700 B2 * | 3/2006 | Dubois et al. | 356/317 |
| 7,697,135 B1 * | 4/2010 | Yarussi | G01J 3/02783 356/326 |
| 8,785,886 B2 * | 7/2014 | Nishikawa et al. | 250/461.2 |
| 2002/0080341 A1 * | 6/2002 | Kosaka | 356/73 |
| 2004/0156098 A1 | 8/2004 | Dubois et al. | |
| 2004/0239932 A1 * | 12/2004 | Brogioli et al. | 356/337 |
| 2005/0185860 A1 * | 8/2005 | Denoue | G06K 9/6212 382/305 |
| 2011/0043607 A1 * | 2/2011 | Grier et al. | 348/40 |
| 2011/0109962 A1 * | 5/2011 | Cui | A61B 5/0059 359/385 |
| 2011/0141273 A1 * | 6/2011 | Dubois | 348/135 |
| 2012/0135535 A1 * | 5/2012 | Grier et al. | 436/164 |
| 2013/0278743 A1 * | 10/2013 | Cheong et al. | 348/79 |

FOREIGN PATENT DOCUMENTS

| | | |
|---|---|---|
| WO | WO 2010/037861 A1 | 4/2010 |
| WO | WO 2011/042442 A1 | 4/2011 |

OTHER PUBLICATIONS

Frank Dubois et al.; Applications of Digital Holographic Microscopes with Partially Spatial Coherence Sources; Journal of Physics: Conference Series 139 (2008) 012027; 2008; 6 pages (1-6); IOP Publishing Ltd.

* cited by examiner

OPTICAL METHOD FOR CHARACTERIZING TRANSPARENT PARTICLES

FIELD OF THE INVENTION

The present invention is related to an optical method for characterising particles.

STATE OF THE ART

Counting small transparent particles in a transparent medium is a well known problem in several technical fields. This may be counting the number of dispersed phase particles in material science, counting the number of cells in a biological culture, counting the number of micelles in a latex in chemistry or in polymer synthesis, . . . .

The first attempt to solve this problem is the use of standard transparent grids (graticules) and then counting manually on a microscope picture the number of particles in each squares defined by the grid. Such manual counting methods suffers from several drawbacks. First of all, it is highly time consuming, it has a poor statistical validity on small numbers and usually has limited reliability.

Therefore, image analysis is sometimes used to automate such counting. In such methods, the microscopic pictures are usually transformed by standard procedure, such as using a threshold level, segmentation, dilatation and erosion transformation, border detection, . . . . The individual particles are then counted by more or less complex algorithms. Such automated methods usually suffer of several drawbacks. For example, if the obtained picture has limited contrast, or in case of overlapping particles, the algorithms may not separate accurately the different particles and the counting has only poor reliability.

Other known methods for counting particles flowing in a liquid are based on shadowing or light diffusion effects. Such methods, widely used for example in the pharmaceutical field also suffers of several drawbacks. First of all, it is usually not possible to discriminate between bubbles and solid particles. This is particularly critical when evaluating cleanliness of physiological buffered solutions, containing large amount of dissolved $CO_2$, perturbating the measurement. In such kind of measurement, no information at all on the nature of the particles can be extracted from the results.

AIMS OF THE INVENTION

The present invention aims to provide a method of characterising and/or counting spheroid transparent particles in a transparent medium that does not present the drawbacks of prior art.

Advantages of the invention will be apparent from the following description.

SUMMARY OF THE INVENTION

The present invention is related to a method for characterising at least one property of transparent objects presenting a focal area (focus point), said object being in a transparent medium, said method comprising the steps of:
illuminating a sample comprising the objects to be characterised by means of a directional light source, thereby inducing light intensity peaks at the focal area of said transparent objects,
determining at least one characteristic of the light intensity peaks,
determining from said at least one characteristic of the light intensity peaks at least one property of said objects.

By transparent object presenting a focal area (focus point), it is meant in the present document an object able to concentrate light at said focal area when illuminated by a directional light source, the concentrated light forming a light intensity peak. In the present invention, said light intensity peaks are directly induced by the interaction between the object and the directional light independently of an imaging device (i.e. the light peaks exist even without being observed).

According to particular preferred embodiments, the method of the present invention comprises one or a suitable combination of at least two of the following features:
  the method further comprises the step of:
    recording a holographic representation of the illuminated sample;
    reconstructing from said holographic representation a three dimensional representation of the light field intensity induced by said sample;
    scanning the three dimensional representation of the light field intensity for determining the light peaks area presenting an intensity higher than a predetermined threshold, each of said light peak corresponding to one particle;
  the at least one objects characteristic comprises the number of said objects, the determined characteristic of the light intensity peaks comprising the number of peaks;
  the objects are selected from the group consisting of gas bubbles, liquid vesicles in an emulsion, solid beads, living cells, dead cells and mixture thereof;
  the objects are selected from the group consisting of living cells, dead cells and mixture thereof;
  said at least one peak characteristic comprises at least one characteristic selected from the group consisting of the distance between the light peak and the corresponding object, the area of the light peak and the light peak intensity;
  the peak characteristic is used to classify said objects into at least two subsets of objects;
  one subset of objects is corresponding to living cells and a second subset of objects is corresponding to dead cells;
  the characterizing method is performed dynamically on successive holographic representation;
  the transparent medium is a flowing liquid transporting the objects;
  the holographic representation is obtained by means of a holographic microscope;
  the microscope is operated according to a differential mode;
  the microscope is operated in a dark field mode;
  the light source is partially coherent;
  the microscope is operated off-axis.

Another aspect of the invention is related to a computer program implementing the method of the invention or a preferred embodiment of the invention.

FIGURE KEYS

Figure 1:
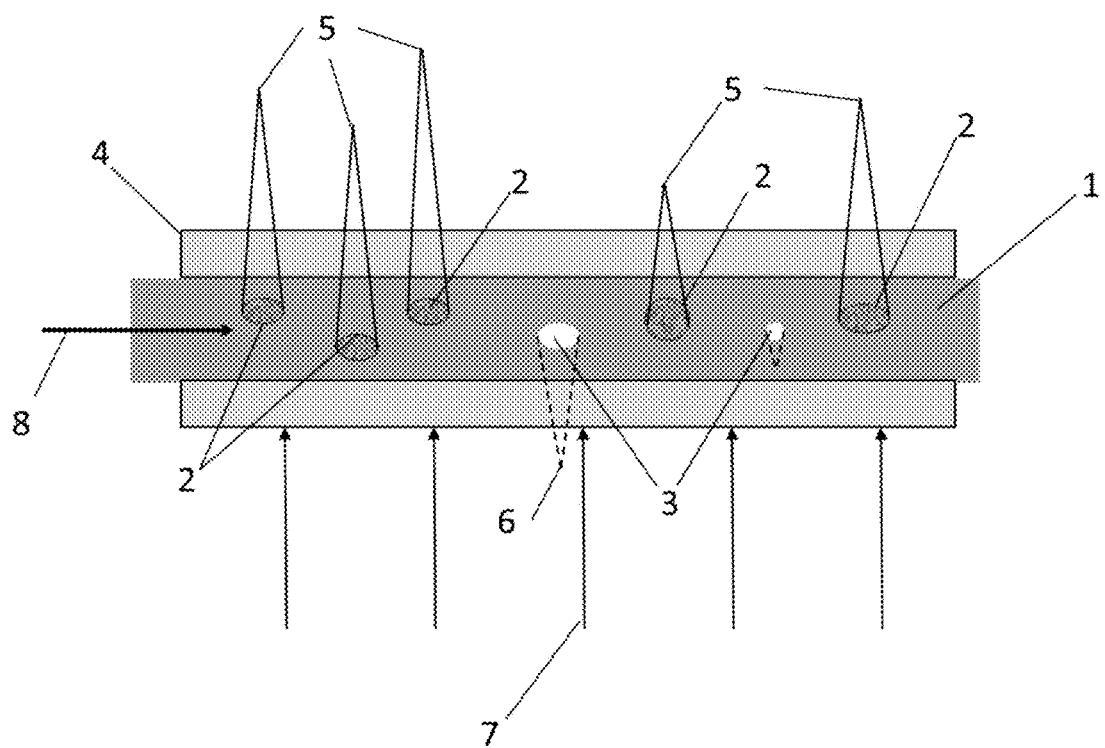
FIG. 1 represents schematically the basic principle of the invention.
Figure 2:
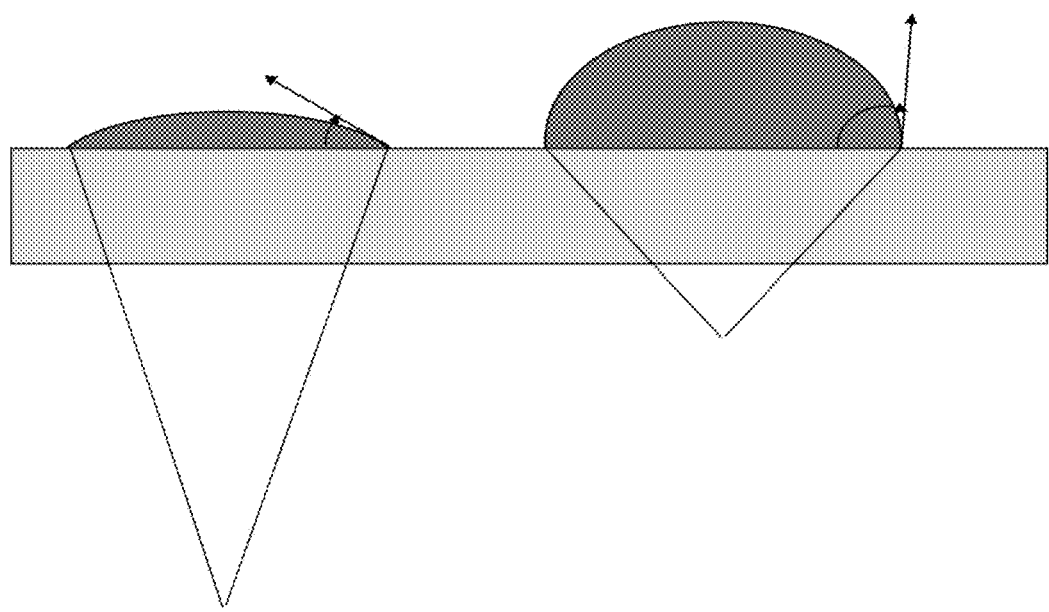
FIG. 2 represents schematically the measurement of contact angles using a method according to the invention.

1: Transparent medium
2, 3: Spheroid transparent objects
4: Transparent walls of the sample container
5, 6: Focal areas of the transparent objects (2,3) that concentrate the illumination light rays (7), forming light intensity peaks.
7: Illumination light rays.
8: Direction of the flow transparent medium

DETAILED DESCRIPTION OF THE INVENTION

The present invention is related to analytical methods using an optical feature common to many transparent objects when illuminated by light. This common feature is that many transparent objects act as a lens, concentrating light on a real focal area behind (5) or on a virtual area ahead (6) of said object.

Such focal area may be induced for example by objects in the form of spheroid or ellipsoid transparent particles (2-3) having a refractive index different from the surrounding medium. Such particles may for example be oil droplets dispersed in an aqueous solution, gas bubbles (3) in a liquid, living or dead cells, liquid droplets in a gaseous flow, . . . .

By transparent, it is meant in the present document, medium maintaining sufficient light directionality to observe focalisation peaks. Such transparency may for example be characterised by haze measurement (ASTM D 1003). The problem arising from high haze is an increase of the light background, and the increased difficulty to discriminate between the background and the peaks.

In order to observe light focalisation intensity peaks, the particles preferably present sizes of more than the incident light wavelength, more preferably larger than three times the light wavelength. In the case of visible light, the particles preferably have dimensions larger than one micrometer.

Transparent particles inducing a focal area are not limited to free flowing spheroid particles, but may also comprise particles trapped on a flat surface, such as liquid droplets or bubbles in contact with glass or the like.

A consequence of the existence of such focal point/area is that each of those particles, when illuminated will produce a light intensity peak which may easily be detected by scanning in three dimensions the light intensity distribution.

Advantageously, the method of the invention is performed by first recording a digital holographic representation of an illuminated sample comprising the particles to be analysed. The scanning and analysis are then preferably performed on a reconstructed 3D representation of the light field induced by the illuminated sample.

Even if a single particle may be characterised by the method of the invention, the possibility of automation of the method renders it particularly suitable for large set of particles. The particles to be characterised may be present simultaneously in the scope of the representation, or may be present in a time sequence.

Preferably, the digital holographic representation is recorded by a digital holographic microscope (DHM). Said DHM may advantageously be of the type described in EP1399730 which is hereby incorporated by reference.

As a preferred alternative, the DHM may be a differential holographic microscope, such as described in EP1631788 which is hereby incorporated by reference.

Advantageously, the DHM is operated in a dark field mode as described in WO/2010/037861. The advantage of such dark field mode is to ease the detection of the light peak by reducing the average light background.

The use of off-axis DHM such as described in the international patent application having number PCT/EP2010/64843 has the advantage of fast recording dynamical events, such as flowing particles in a fluid.

Preferably, the light peak intensity is determined by detecting light intensity above a predetermined threshold in the volume of the 3D representation.

A first application of such focalisation point determination, is a method for counting spheroid particles in a flowing medium. In such a method, the number of light peak intensity is corresponding to the number of spheroid particles in the sample. An advantage of such a counting method is that the focused light area is much smaller than the particle size, so that even in case of high density of particles, the light peaks will be easily resolved and well separated. This is a key advantage over counting method of overlapping particles in a 2D representation.

Counting particles is only using the detection of the peaks, but other characteristics of the light peak, such as shape, intensity and position may also advantageously be used. Such information are characteristics of the lens equivalent to each particle. Those lenses characteristics are themselves determined by the geometrical shape and refractive index of the particles.

For example, gas bubbles in a liquid will act as diverging lenses, giving rise to focal points ahead of the bubbles, contrary to a high refractive index particle which will act as a converging lens, giving rise to a focal point behind the particle. Therefore, in a preferred method, the particles are classified according to the relative position of the corresponding light peak area. This classification permits to easily discriminate between different class of particles such as bubbles and high refractive index particles.

By high or low refractive index, it is meant in the present document respectively refractive index higher or lower than the refractive index of the medium surrounding the particles.

As another example of particles differing by their optical properties, it has surprisingly been shown that the method of the present invention was able to discriminate between dead and living cells flowing in a liquid medium based on characteristics of the light peaks corresponding to the cells.

Figure 5:
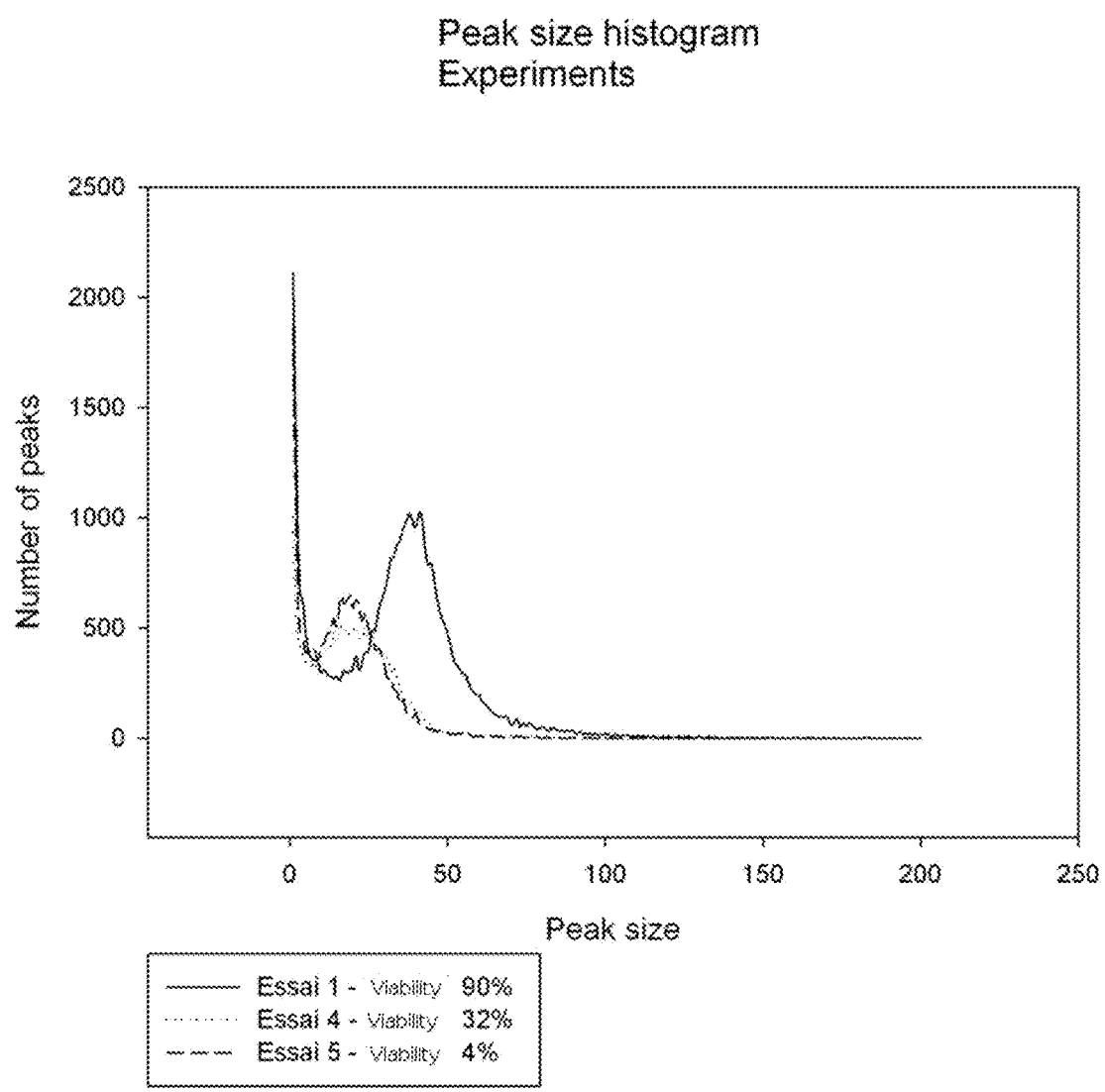
FIG. 5 represents a histogram of the peak number as a function of the peak sizes (areas) of a cell culture before and after thermal treatments inducing cellular death.

In the experimental example shown hereafter, as shown in FIG. 5 the size of the peak was used as the discriminating criteria (i.e. the volume or area wherein the light intensity is higher than the threshold). It was also discovered that other criteria could be used, such as the absolute intensity of the peak (i.e. the maximum intensity or the integral of the light intensity within the peak).

As the method may easily be automated and performed automatically on consecutive time series, the method of the invention may advantageously be used to study the displacement of individual cells.

As a further dynamical application of the invention, spray drying process may be studied, using several peak characteristics. In such studies, the sprayed particles are counted by the method described here above, their individual movements in the flow may be accurately determined, the size of the particle as a function of time may simultaneously be determined by analysing the reconstructed particle ("in focus" image) and the concentration of the solution may be calculated from the particle refractive index, determined from the correlation between the shape of the particle and the light intensity peak position at the focal area. One of the advantages brought by such method would be for example the ability of determining supersaturation phenomenon and the corresponding nucleation and growth processes.

Another advantageous application of the determination of the focal point of transparent object is the accurate determination of geometrical parameters of liquid droplets on a transparent flat surface. Those geometrical parameters may then be used to accurately calculate for example contact angles.

More generally, the following parameters may be of interest: number of peaks, peaks shapes and sizes, peaks intensities (integral and/or maximum value), relative positions from corresponding particles.

Those peaks parameters may advantageously be correlated with the shape and position of the corresponding particle.

Correlations with corresponding fluorescence data originating from the particles may also advantageously be used to characterise the particles. Such fluorescence correlation may use the method described in document US 2004/156098 which is incorporated hereby by reference.

From those parameters, the following characteristics may advantageously be inferred: viability of living cells, solution concentration, type of cells, particle motion, etc.

EXAMPLE

Cell cultures have been characterised using the method of the present invention.

Figure 3:
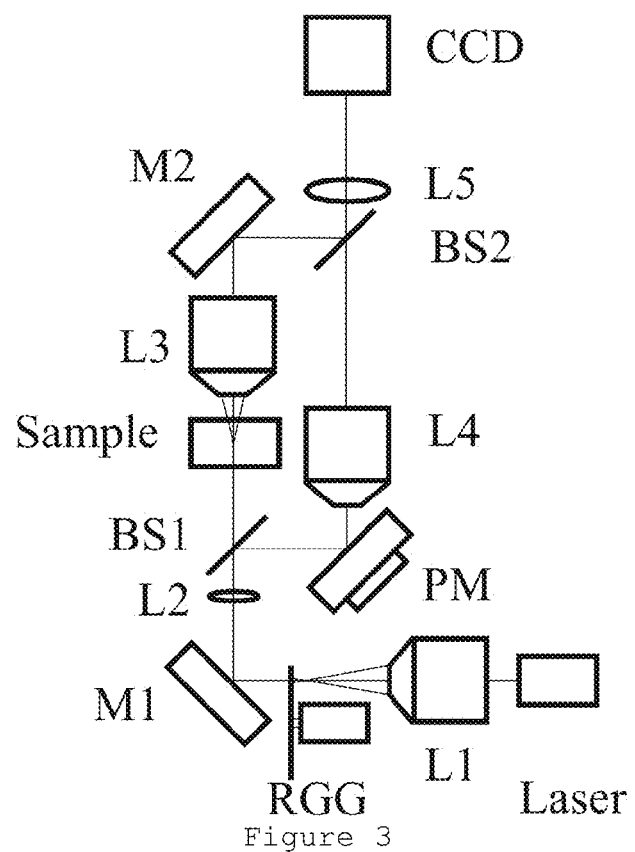
FIG. 3 represents schematically the digital holographic microscope used to generate the data of the examples.

A microscope as represented in FIG. 3 was used to record digital holograms. The hologram sampling rate was 2.5 Hz, and 200 holograms where taken in a sequence.

As represented in FIG. 1, the sample holder 4 was a flow cell wherein the liquid samples were in a flow 8 and the particles were dynamically observed.

Figure 4A:
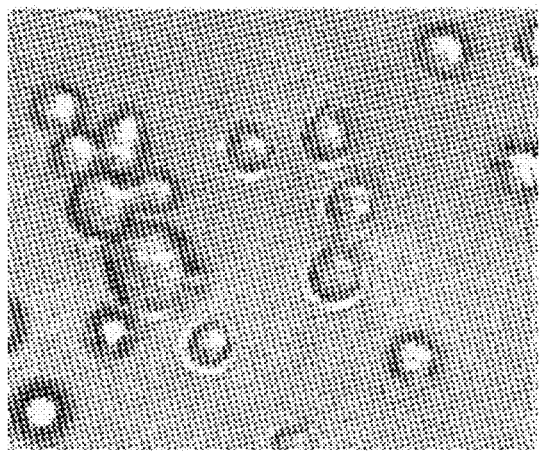
FIG. 4a represents an "in focus" intensity image of living cells.
Figure 4B:
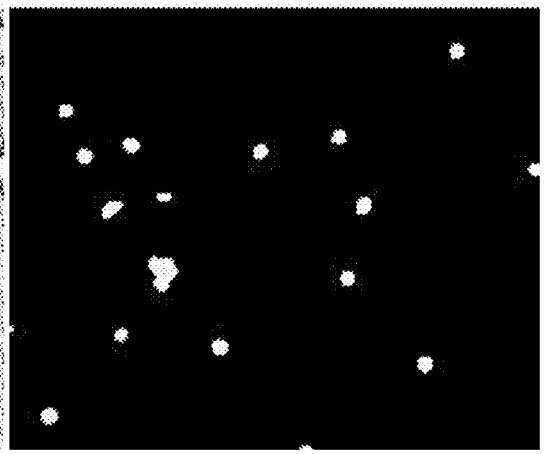
FIG. 4b Represents the focal areas of the transparent cells of FIG. 4-a that concentrate the illumination light rays, forming light intensity peaks

FIG. 4a represents a reconstructed picture of one of the obtained holographic record. FIG. 4b represents the corresponding projection of the focalisation peaks. It can be seen in FIG. 4b that even contacting cells are well resolved when considering the light peak instead of the corresponding cells representation. Notice that for the ease of representation, the peaks have been represented in two dimensions. In the real representation, they are also resolved in depth.

The number of cells as determined by the present method was 3.72 millions of cells/ml. In comparison, manual counting in a bürker counting cell was 3.71 millions of cells/ml. This very good agreement was confirmed even in the case of very high cells concentration. In this last case, usual automated counting methods give inaccurate results.

In a further experiment, the method of the invention was first used to count the number of cells in a culture. In a second step, the culture medium was submitted to a 3 h thermal treatment at 42.5° C. Such a treatment is known to reduce viability of the cells.

The distribution of the observed light peak size was then determined before and after the thermal treatment. The results are shown in FIG. 5. As can be seen in that figure, the peak size distribution is strongly correlated to the viability of the cells.

The invention claimed is:

1. Method for characterizing transparent objects (2,3) in a transparent medium (1), said transparent objects (2,3) presenting an optical focal area (5,6) said method comprising the steps of:
   illuminating a sample comprising the objects (2,3) to be characterized by means of a directional light (7) source thereby inducing light intensity peaks (5,6) at the focal area of said transparent objects;
   wherein said focal area being a real focal area behind (5) said objects or a virtual focal area ahead (6) of said objects (2,3);
   determining at least one characteristic of the induced light intensity peak (5,6),
   determining from said at least one characteristic of the light intensity peak (5,6) at least one property of said object (2,3).

2. Method according to claim 1 further comprising the steps of:
   recording an holographic representation of the illuminated sample;
   reconstructing from said holographic representation a three dimensional representation of the light field intensity induced by said sample;
   scanning the three dimensional representation of the light field intensity for determining the light intensity peaks (5,6) presenting an intensity higher than a predetermined threshold, each of said light intensity peak (5,6) corresponding to one object (2,3).

3. Method according to claim 2 wherein the holographic representation is obtained by means of a holographic microscope.

4. Method according to claim 3 wherein said microscope is operated according to a differential mode.

5. Method according to claim 3 wherein said microscope is operated in a dark field mode.

6. Method according to claim 3 wherein said light source is partially coherent.

7. Method according to claim 6 wherein said microscope is operated off-axis.

8. Method according to claim 1 wherein the at least one particles characteristic comprises the number of said objects.

9. Method according to claim 1 wherein said objects are selected from the group consisting of gas bubbles, liquid vesicles in an emulsion, solid beads, living cells, dead cells and mixture thereof.

10. Method according to claim 1 wherein said objects are selected from the group consisting of living cells, dead cells and mixture thereof.

11. Method according to claim 1 wherein at least one peak characteristic is determined, said peak characteristic being selected from the group consisting of the distance between the light intensity peak and the corresponding object, the area of the light intensity peak and the intensity of the light intensity peak.

12. Method according to claim 11 wherein said peak characteristic is used to classify said objects into at least two subsets of objects.

13. Method according to claim 12 wherein one subset of objects corresponds to living cells and a second subset of objects corresponds to dead cells.

14. Method according to claim 1 wherein said characterizing method is performed dynamically on successive holographic representation.

15. The method of claim 1, wherein the transparent object has sufficient light directionality to observe focalization peaks.

16. The method of claim 1, wherein the transparent objects are spheroidal;
wherein the transparent medium is flowing;
wherein the at least one characteristic of the induced light intensity peaks is the number of the induced light intensity peaks;
wherein the at least one characteristic of said object is the number of the spheroidal objects.

17. A computer program recorded on a non-transitory computer readable media for counting transparent objects presenting an optical focal area from a digital holographic representation of a transparent sample comprising said objects, said computer program when loaded on a computer determining the number of light intensity peaks in the holographic representation; and
wherein said focal area being a real focal area behind (5) said objects or a virtual focal area ahead (6) of said objects (2,3).

18. Method for characterizing transparent objects (2,3) in a transparent medium (1), said transparent objects (2,3) presenting an optical focal area (5,6) said method comprising the steps of:
illuminating a sample comprising the objects (2,3) to be characterized by means of a directional light (7) source thereby inducing light intensity peaks (5,6) at the focal area of said transparent objects;
determining at least one characteristic of the induced light intensity peak (5,6),
determining from said at least one characteristic of the light intensity peak (5,6) at least one property of said object (2,3);
wherein the transparent object is located observed at a first focal distance and the light intensity peak is observed at a second focal distance; and
wherein the first focal distance is greater than the second focal distance; or
wherein the second focal distance is greater than the first focal distance, such that a real focal area is located at a focal distance behind the transparent object or a virtual focal area is located at a focal distance in front of the transparent object.

19. The method of claim 18, further comprising recording data from the real focal area that is located behind the transparent object and not in the image plane of the transparent object or recording data from the virtual focal area that is located in front the transparent object not in the image plane of the transparent object.

* * * * *